US011167096B2

(12) United States Patent
Silver et al.

(10) Patent No.: US 11,167,096 B2
(45) Date of Patent: Nov. 9, 2021

(54) FILTER CARTRIDGE ASSEMBLIES FOR MANAGING FLUID AND HUMIDITY IN ENDOSCOPIC SURGERY

(71) Applicant: Conmed Corporation, Utica, NY (US)

(72) Inventors: Mikiya Silver, New Haven, CT (US); Michael J. Kane, Clinton, CT (US)

(73) Assignee: Conmed Corporation, Utica, NY (US)

( * ) Notice: Subject to any disclaimer, the term of this patent is extended or adjusted under 35 U.S.C. 154(b) by 323 days.

(21) Appl. No.: 16/017,125

(22) Filed: Jun. 25, 2018

(65) Prior Publication Data

US 2019/0388631 A1  Dec. 26, 2019

(51) Int. Cl.
*A61B 17/34* (2006.01)
*B01D 46/00* (2006.01)
*B01D 46/10* (2006.01)
*B01D 46/52* (2006.01)
*A61B 1/015* (2006.01)
*A61M 13/00* (2006.01)

(52) U.S. Cl.
CPC ....... *A61M 13/006* (2014.02); *A61B 17/3421* (2013.01); *B01D 46/0008* (2013.01);
(Continued)

(58) Field of Classification Search
CPC ............ B01D 46/10; B01D 46/0024; B01D 46/0008; B01D 46/521; A61M 13/006; A61M 2202/02; A61M 2202/0225; A61M 2205/3344; A61M 2202/005; A61M 2202/0007; A61M 2202/0014; A61M 2205/3331; A61M 2205/7536; A61M 16/0808; A61M 2205/07; A61M 2210/1021; A61M 2210/1064;
(Continued)

(56) References Cited

U.S. PATENT DOCUMENTS 4,963,134 A * 10/1990 Backscheider ..... A61M 1/0023
                                                        55/467
7,182,752 B2    2/2007 Stubbs et al.
(Continued)

FOREIGN PATENT DOCUMENTS

KR      101761170 B1    7/2017
WO      2016137640 A1   9/2016
WO      2018039239 A1   3/2018

OTHER PUBLICATIONS

International Search Report and Written Opinion issued in corresponding PCT Application No. PCT/US2019/035760 dated Oct. 1, 2019.

*Primary Examiner* — Lauren P Farrar
*Assistant Examiner* — Hamza A Darb
(74) *Attorney, Agent, or Firm* — Locke Lord LLP; Scott D. Wofsy; Joshua L. Jones

(57) ABSTRACT

A filter cartridge for surgical gas delivery systems includes a filter housing configured to be seated in a filter cartridge interface of a surgical gas delivery system, with a plurality of flow paths defined through the filter housing including at least one evacuation/return flow path and at least one insufflation/sensing flow path. A humidity filter element is included in the evacuation/return flow path for removing humidity from an evacuation/return lumen of a tube set. The humidity filter element can include a sintered polymer material configured to provide tortuous flow paths therethrough to condense humidity out of a flow through the humidity filter element.

16 Claims, 9 Drawing Sheets

(52) U.S. Cl.
CPC ..... *A61B 17/3474* (2013.01); *A61B 2218/008* (2013.01); *A61M 2205/3331* (2013.01)

(58) Field of Classification Search
CPC .. A61M 2210/1007; A61M 2205/7527; A61M 2205/3379; A61M 2205/505; A61M 25/003; A61M 16/08; A61M 2205/75; A61M 13/00; A61B 17/3474; A61B 2218/008; A61B 2217/005; A61B 17/3421; A61B 1/313; A61B 1/015
See application file for complete search history.

(56) References Cited

U.S. PATENT DOCUMENTS

| | | | |
|---|---|---|---|
| 7,285,112 B2 | 10/2007 | Stubbs et al. | |
| 7,338,473 B2 | 3/2008 | Campbell et al. | |
| 7,413,559 B2 | 8/2008 | Stubbs et al. | |
| 7,854,724 B2 | 12/2010 | Stearns et al. | |
| 9,067,030 B2 | 6/2015 | Stearns et al. | |
| 9,526,886 B2 | 12/2016 | Mastri et al. | |
| 9,950,127 B2 | 4/2018 | Stearns et al. | |
| 2005/0107767 A1* | 5/2005 | Ott | A61M 31/00 604/500 |
| 2009/0044810 A1* | 2/2009 | Kwok | A61M 16/0633 128/206.28 |
| 2013/0231606 A1* | 9/2013 | Stearns | A61M 13/006 604/26 |
| 2015/0202391 A1 | 7/2015 | Stearns et al. | |
| 2016/0000459 A1* | 1/2016 | Palmerton | A61B 90/30 604/541 |
| 2016/0287817 A1* | 10/2016 | Mastri | A61M 5/165 |
| 2017/0000959 A1 | 1/2017 | Mantell et al. | |
| 2017/0050011 A1 | 2/2017 | Zergiebel et al. | |

* cited by examiner

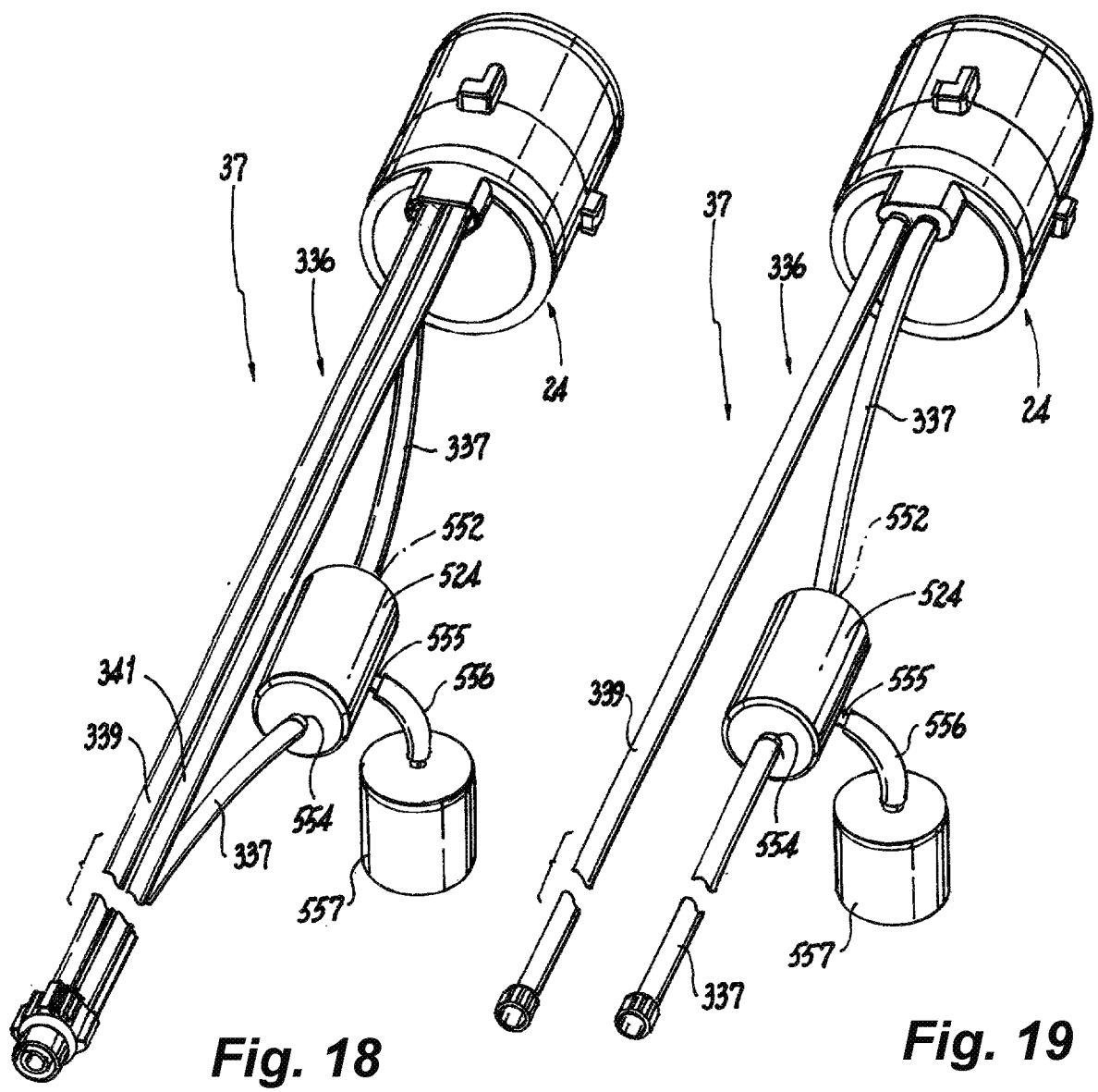
Fig. 18  Fig. 19
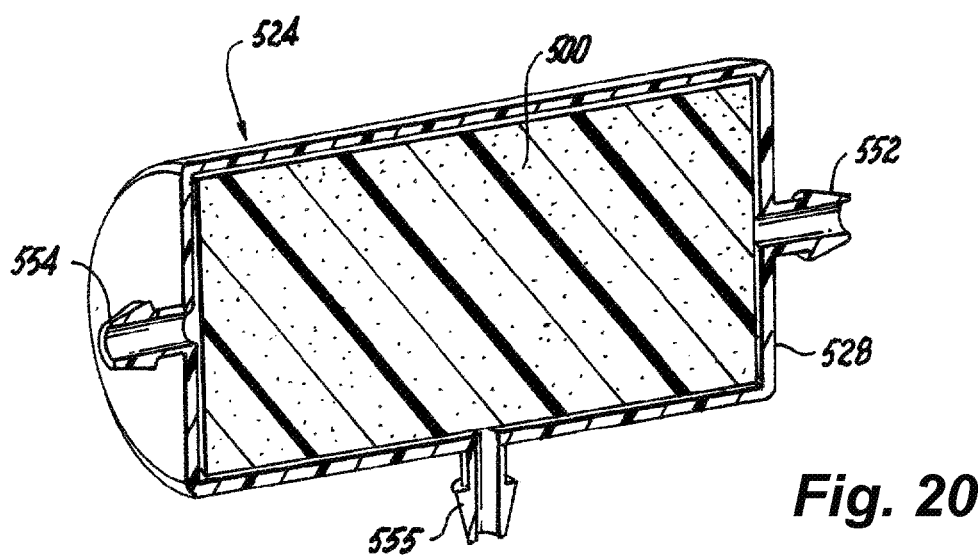
Fig. 20

FILTER CARTRIDGE ASSEMBLIES FOR MANAGING FLUID AND HUMIDITY IN ENDOSCOPIC SURGERY

BACKGROUND OF THE INVENTION

1. Field of the Invention

The subject invention is directed to endoscopic surgery, and more particularly, to filter systems and methods for a multimodal insufflation system used during endoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical insufflation systems and smoke evacuation systems are known in the art.

Additionally, CONMED Corporation of Utica, N.Y., USA has developed surgical access devices that permit access to an insufflated surgical cavity without conventional mechanical seals, and has developed related systems for providing sufficient pressure and flow rates to such access devices, as described in whole or in part in U.S. Pat. No. 7,854,724.

The present disclosure relates to multimodal systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids, such as with the above-mentioned surgical access devices described in U.S. Pat. No. 7,854,724, as well as those in U.S. Pat. Nos. 7,182,752, 7,285,112, 7,413,559 or 7,338,473, for example.

Use of a single multimodal system such as those described herein reduces costs by requiring purchase of only one system while achieving multiple functions, and also thereby reduces the amount of equipment needed in an operating room, thus reducing clutter and allowing space for other necessary equipment.

While the preceding discussion makes particular mention of laparoscopy and abdominal insufflation, those skilled in the art will readily appreciate that the issue of managing fluid and humidity is generally relevant for insufflation of any suitable surgical cavity, including colorectal and thoracic insufflation.

In devices like smoke evacuation devices that recirculate or remove gas from a patient cavity, even gas that is filtered for particulate and fluids can carry moisture as gaseous water vapor. The water vapor can condense inside the device and potentially damage electrical components, rubber seals in valves and pumps, and corrode metal components. The fluid can also potentially damage or alter sensor readings when condensing on various surfaces inside a device. The presence of humidity can also facilitate the growth of bacteria and fungi which needs to be avoided in a multi-patient medical device. Removing humidity from the evacuation/return lumen feeding into the device can help prevent the growth of bacteria and fungi, as well as reducing the damage to electrical components, rubber seals, metal components, and sensors in the device.

The conventional techniques have been considered satisfactory for their intended purpose. However, there is an ever present need for improved filtration in surgical access devices. This disclosure provides a solution for this problem.

SUMMARY OF THE INVENTION

A filter cartridge for surgical gas delivery systems includes a filter housing configured to be seated in a filter cartridge interface of a surgical gas delivery system, with a plurality of flow paths defined through the filter housing including at least one evacuation/return flow path and at least one insufflation/sensing flow path. A humidity filter element is included in the evacuation/return flow path for removing humidity from an evacuation/return lumen of a tube set.

The humidity filter element can include a sintered polymer material configured to provide tortuous flow paths therethrough to condense humidity out of a flow through the humidity filter element. Each of the first and second filter elements can include a pleated filter material. A first filter element can be seated in a first end portion of the filter housing, and a second filter element can be seated in a second end portion of the filter housing opposite the first end portion. An activated carbon filter element can optionally be seated in the filter housing between the humidity filter element and the second filter element. The cover plate can include a fitting for connecting to a tri-lumen tube set for communication of gases between a tri-lumen tube set and the filter elements, and a tri-lumen tube set connected to the fitting. It is also contemplated that the cover plate can include a fitting for connecting to a bi-lumen tube set for communication of gases between a bi-lumen tube set and the filter elements, and a bi-lumen tube set connected to the fitting.

The humidity filter element can be seated in a return passage of the filter housing radially outboard of the first filter element. The humidity filter element can have a cross-sectional shape that conforms to the return passage of the filter housing. The cross-sectional shape of the humidity filter element can include an inner radiused portion and an outer radiused portion, wherein the inner and outer radiused portions are non-concentric. The cross-sectional shape of the humidity filter element can include a circumferentially spaced apart set of radial ends.

It is also contemplated that the humidity filter element can be seated in the filter housing between the first and second filter elements. A separator wall can be included within the filter housing between the humidity filter element and the second filter element. The separator wall can include a gas aperture therethrough, wherein a fluid trap is defined between the first filter element and the separator wall, wherein the gas aperture is configured to allow passage of gas above a reservoir of fluid trapped in the fluid trap. The filter housing can include at least one optical prism formed integral with the housing within the reservoir for sensing level of a liquid in the reservoir. The humidity filter element and the separator wall can be keyed to one another for circumferential alignment. The humidity filter element can define a notch along one side thereof for accommodating at least one optical prism formed integral with the housing within the reservoir for sensing level of a liquid in the reservoir.

A tube set assembly for surgical gas delivery systems includes a filter cartridge with a filter housing configured to be seated in a filter cartridge interface of a surgical gas delivery system, with a plurality of flow paths defined through the filter housing including at least one evacuation/return flow path and at least one insufflation/sensing flow path. A tube set includes a first lumen in fluid communication with the evacuation/return flow path and a second lumen in fluid communication with the insufflation/sensing flow path. An in-line humidity filter assembly with a humidity filter housing defines an inlet in fluid communication with a first portion of the first lumen for receiving gas from a patient and an outlet in fluid communication with a second portion of the first lumen for communication of humidity filtered gas from the in-line humidity filter assembly to the filter cartridge. A humidity filter element is seated in the humidity filter housing for removing humidity from the first lumen of the tube set.

The tube set can be a bi-lumen tube set. It is also contemplated that the tube set can be a tri-lumen tube set, or can have any other suitable number of lumens.

The humidity filter element can include a sintered polymer material configured to provide tortuous flow paths therethrough to condense humidity out of a flow through the humidity filter element. The humidity filter element can be in-line between the inlet and the outlet of the humidity filter housing. A sponge element can be included within the humidity filter housing offset from being in-line between the inlet and outlet of the humidity filter housing for absorbing condensation from the humidity filter element.

The humidity filter element can be a planar layer, and wherein the sponge element can be a planar layer in parallel with the humidity filter element. The humidity filter element can be cylindrical, and the sponge element can be an annular layer arranged around the humidity filter element. The humidity filter housing can include a drain for removal of condensation from the humidity filter housing, wherein the humidity filter housing includes only the humidity seal element and is devoid of a separate sponge element.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 18 is a perspective view of an exemplary embodiment of a humidity filter assembly constructed in accordance with the present disclosure, showing the humidity filter assembly connected in-line with one lumen of a tri-lumen tube set connected to a filter cartridge for connecting to a filter cartridge interface as shown in FIG. 1;

FIG. 19 is a perspective view of the humidity filter assembly of FIG. 18, showing the humidity filter assembly connected in-line with one lumen of a bi-lumen tube set connected to a filter cartridge for connecting to a filter cartridge interface as shown in FIG. 1; and FIG. 20 is a cross-sectional perspective view of the humidity filter assembly of FIG. 18, showing the humidity filter element and the drain without a sponge element.

DETAILED DESCRIPTION OF THE PREFERRED EMBODIMENTS

Figure 1:
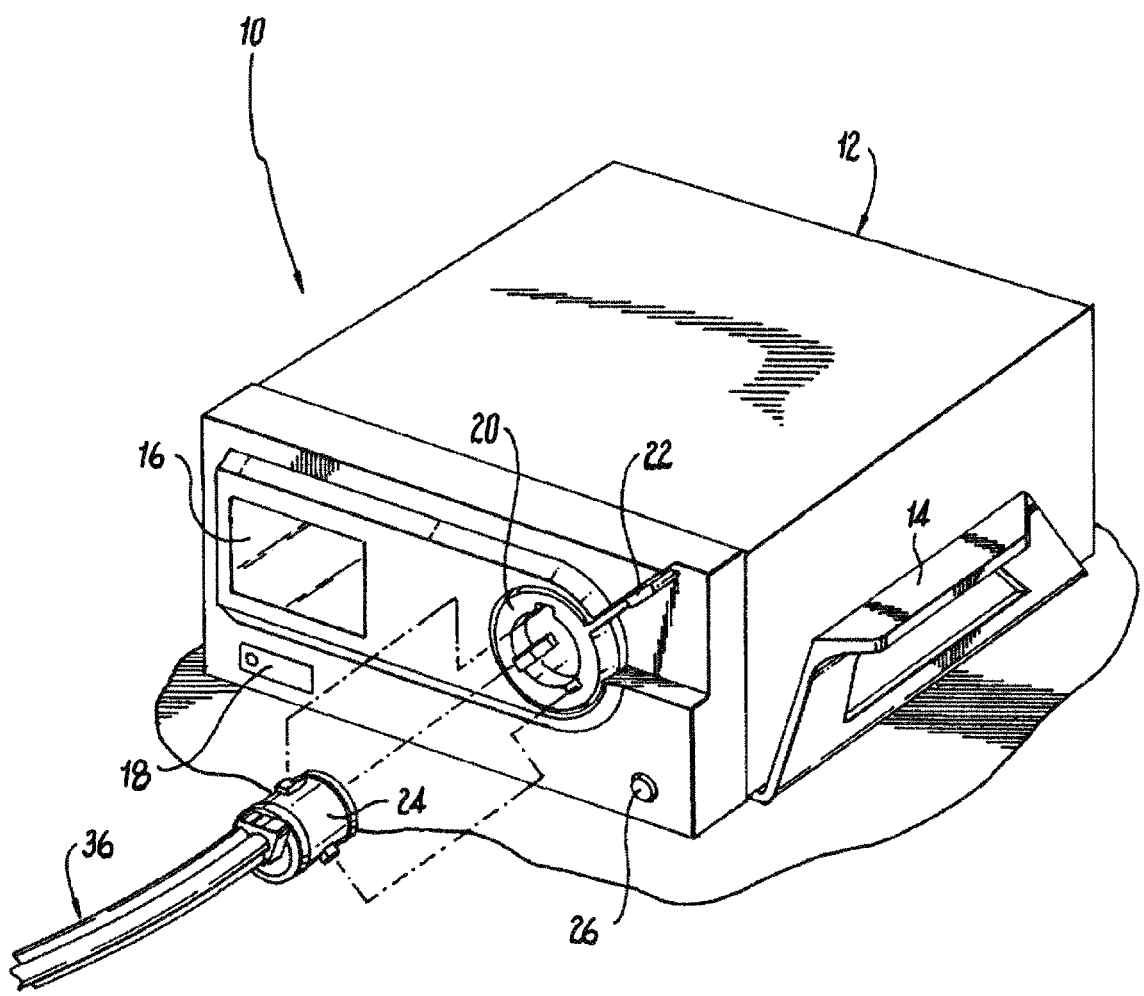
FIG. 1 is a perspective view of a multimodal gas delivery device, showing the filter cartridge and the corresponding filter cartridge interface constructed in accordance with an exemplary embodiment of the subject invention.

Reference will now be made to the drawings wherein like reference numerals identify similar structural features or aspects of the subject disclosure. For purposes of explanation and illustration, and not limitation, a partial view of an exemplary embodiment of a filter cartridge in accordance with the disclosure is shown in FIG. 1 and is designated generally by reference character 24. Other embodiments of filter cartridges in accordance with the disclosure, or aspects thereof, are provided in FIGS. 2-20, as will be described. The systems and methods described herein can be used for filtering humidity out of surgical gases such as smoke evacuation gas from a surgical cavity during smoke-producing surgical procedures.

There is illustrated in FIG. 1 a surgical gas delivery system 10 for use during endoscopic surgical procedures. The system 10 includes a device housing 12 with carrying handles 14 on each side of the housing. The front face of the housing 12 has a capacitive or resistive touch screen 16 for presenting a graphical user interface (GUI) and a power switch 18 for turning the device on and off.

The front face of housing 12 further includes a filter cartridge interface 20 with a rotatable latch mechanism 22 configured to facilitate the secure engagement of a disposable filter cartridge 24 within the device housing 12. In addition, the front face of housing 12 includes a standard 6 mm insufflation connection 26. While not shown, the rear face of the housing 12 includes a gas supply fitting for connection with a source of compressed gas, a standard USB interface for service purposes, and a standard power connection.

The filter cartridge interface 20 is designed to recognize which type of filter 24 has been inserted into the housing. For example, it may recognize the proper position or orientation of the filter cartridge. It can also recognize if the inserted filter is specifically designed for use in the first mode of operation (i.e., the gaseous seal mode) or a filter specifically designed for use in the second mode of operation (i.e., insufflation and smoke evacuation mode). Other aspects of surgical gas delivery systems are described in U.S. Pat. No. 9,067,030, which is incorporated by reference herein in its entirety. Filter cartridge and/or tube set recognition can be accomplished, for example, using RFID techniques.

Figure 2:
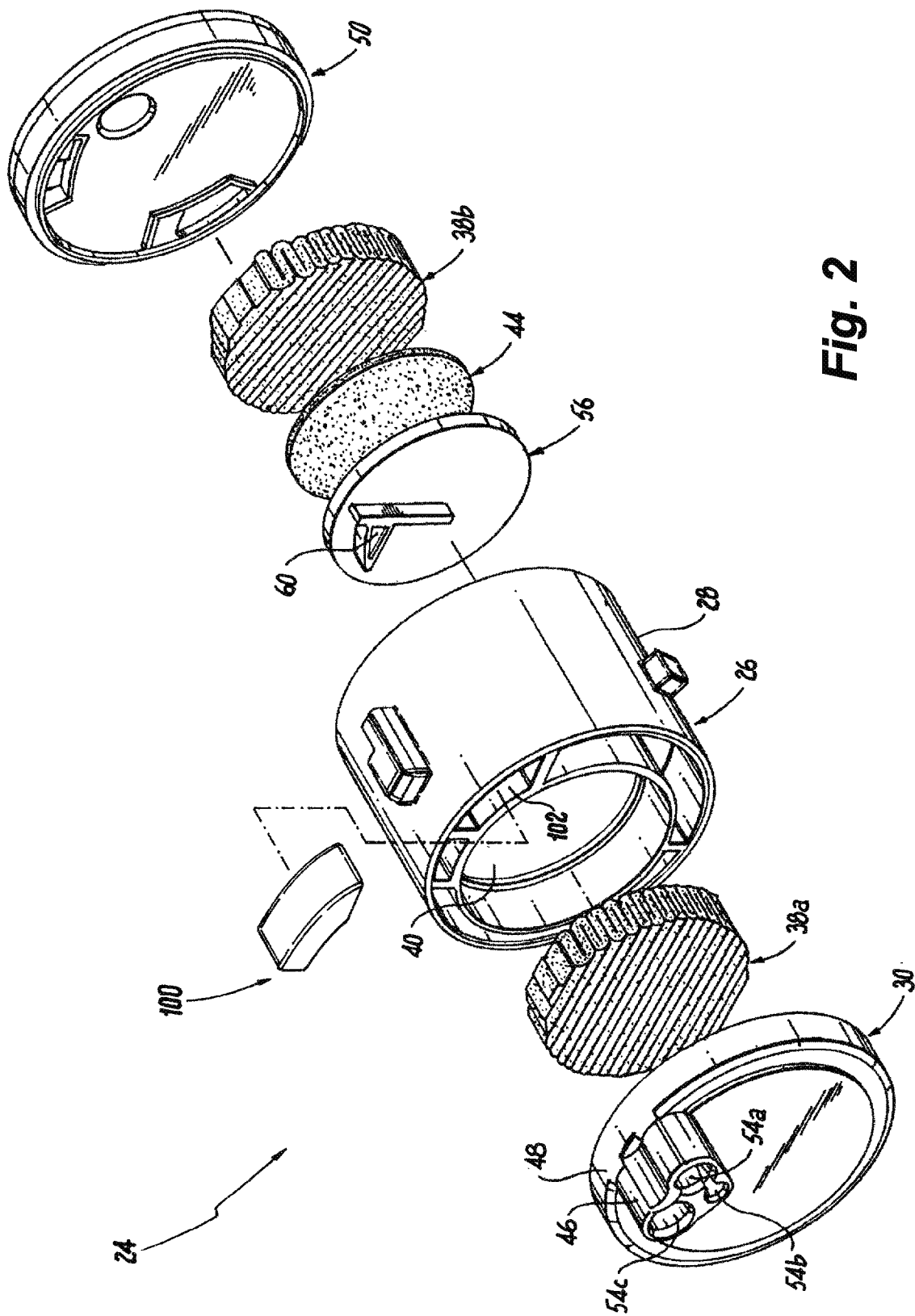
FIG. 2 is an exploded perspective view of a filter cartridge adapted and configured for interfacing with the gas delivery device of FIG. 1, showing the filter cartridge components looking toward the openings in the fitting for the tri-lumen-tube set in the first cover plate.

Referring to FIG. 2, the filter cartridge 24 has a filter housing 28 that includes a first cover plate 30 having a fitting 46 associated with a tri-lumen tube set 36 (as shown in FIG. 1). The filter cartridge 24 is configured to be seated in the filter cartridge interface 20 of the surgical gas delivery system 10 of FIG. 1. The filter housing 28 is dimensioned and configured to support a pair of first and second pleated filter elements 38a and 38b, and it defines an interior reservoir or fluid trap 40 for collecting liquid that has been drawn into the system through the suction line of the tube set 36 during smoke evacuation, for example.

Figure 3:
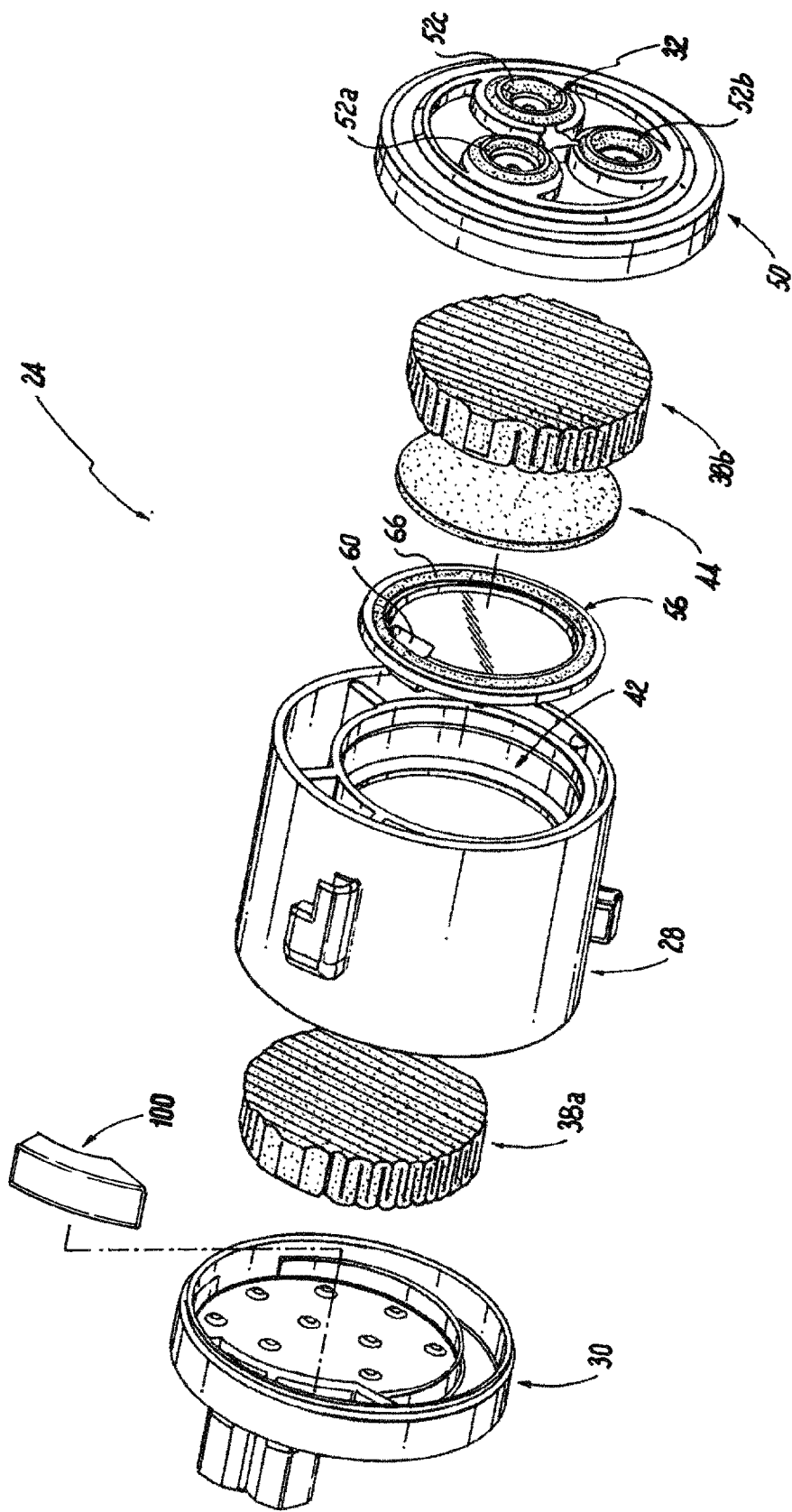
FIG. 3 is an exploded perspective view of the filter cartridge of FIG. 1, showing the filter cartridge components looking toward the apertures in the second cover plate that seal against the gas ports in the filter cartridge interface of FIG. 1.
Figure 4:
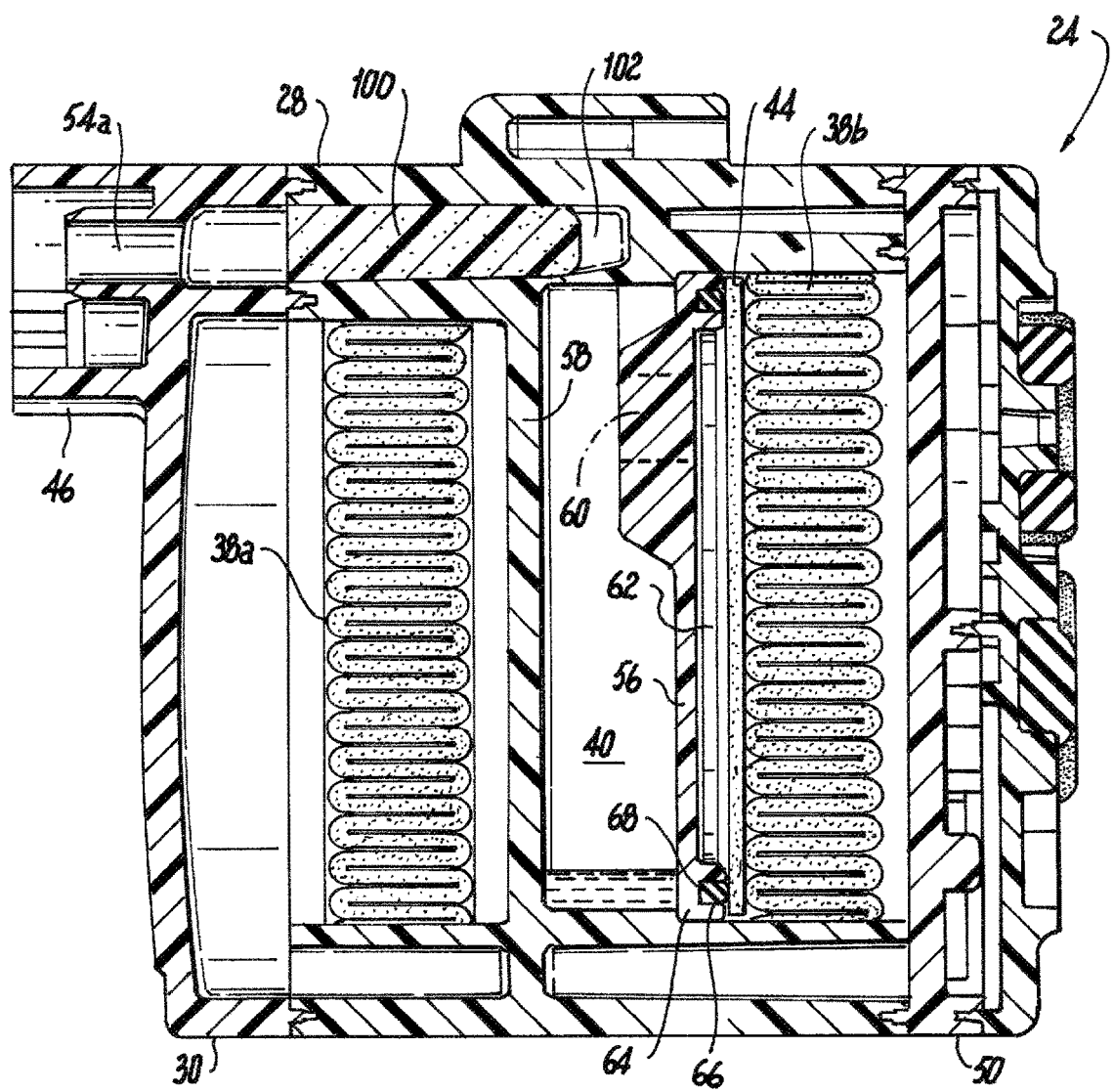
FIG. 4 is a cross-sectional side elevation view of the filter cartridge of FIG. 1, showing the filter elements assembled into the filter housing.

The first filter element 38a is seated in a first end portion 26 of the filter housing 28. As shown in FIG. 3, the second filter element 38b is seated in a second end portion 42 of the filter housing 28 opposite the first end portion 26. An optional third filter element 44 can seated in the filter housing 28 between the first and second filter elements 38a and 38b, as shown in FIG. 4. There is a fourth filter element 32 within end cap 50, shown in FIG. 3, that is a non-pleated filter for the sense/insufflation line described below. The optional third filter element 44 includes an activated carbon material and is in the form of an activated carbon disc. Each of the first and second filter elements 38a and 38b includes a pleated filter material. The third filter element 44 is a separate filter element from the second and third filter elements 38a and 38b, but it is contemplated that it could be integrated together with the second filter element 38b. For example, a mesh support can be sandwiched between a paper filter and a carbon filter together that can then be folded into pleats to form combined second filter element 38b and third filter element 44.

The first cover plate 30 is mounted to a first end of the filter housing 28 to secure the first filter element 38a in the first end portion 26 of the filter housing 28. The first cover plate 30 includes a fitting 46 for connecting to the tri-lumen tube set 36 of FIG. 1 for communication of gases between a tri-lumen tube set 36 and the filter elements 38a, 38b, and 44. A second cover plate 50 is mounted to the opposite end of the filter housing 28 to secure the second filter element 38b in the second end portion 42 of the filter housing. The second cover plate 50 includes a proximal and a distal plate welded or otherwise joined together with the fourth filter element 32 sandwiched therebetween. Referring to FIG. 3, the second cover plate 50 defines three apertures 52a, 52b, and 52c that are each configured to seal against three respective gas ports defined in the filter cartridge interface 20 of FIG. 1. Fitting 46 includes three corresponding openings 54a, 54b, and 54c.

A first flow path is defined through filter cartridge 24 from opening 54a, through to fluid trap 40 (as indicated with broken lines in FIG. 4) and on through the second and third filter elements 38b and 44 and out through aperture 52a for filtration of smoke evacuation gas from a patient, through one of lumens in the tri-lumen tube set 36 into the surgical gas delivery system 10 of FIG. 1. The second filter element 38b is downstream of the third filter element 44 in this first flow path.

A second flow path is defined through the filter cartridge 24, that is fluidly isolated within the filter cartridge 24 from the first flow path. The second flow path brings gas from the surgical gas delivery system 10, through aperture 52b, through the first filter element 38a, and out opening 54b for maintaining a cavity pressure with gas through a second one of the lumens in the tri-lumen tube set 36. The first filter element 38a is therefore in a separate flow path from the second and third filter elements 38b and 44. This second flow path is in the pressure line, supplying pressure to jets to create a gas seal in a valve-less seal, e.g., for a surgical access device connected to the tri-lumen tube set 36.

A third flow path is defined through the filter cartridge 24 that is fluidly isolated within the filter cartridge 24 from the other two flow paths. This third flow path does not pass through any of the filter elements 38a, 38b, or 44. Instead, the third flow path communicates pressure from opening 54c through the filter cartridge 24 to aperture 52c, bypassing the filter elements 38a, 38b, and 44 so the surgical gas delivery system 10 can monitor pressure, e.g., in a surgical cavity, through a third one of the lumens in the tri-lumen tube set 36. $CO_2$ insufflation gas can flow from aperture 52c to opening 54c to a surgical cavity. This third flow path acts as the insufflation/sense line, and is the only one of the three flow paths that passes through the fourth filter element 32.

With reference now to FIG. 4, a separator wall 56 is included within the filter housing 28 between the first filter element 38a and the second filter element 38b. The separator wall 56 cooperates with a bulkhead 58 of filter housing 28 inboard of first filter element 38a to define the fluid trap 40 therebetween for trapping fluids (shown schematically in FIG. 4 in the bottom of the fluid trap 40) from incoming gas evacuated from the surgical cavity. The separator wall 56 includes a gas aperture 60 therethrough. The gas aperture 60 is configured to allow passage of gas above a reservoir of fluid trapped in the bottom of fluid trap 40.

A plenum 62 is defined between the separator wall 56 and the third filter element 44. The gas aperture 60 is configured to pressurize the plenum 62 with gas for utilization of a larger cross-sectional area of the third filter element 44 than the cross-sectional area of the gas aperture 60, i.e. the plenum 62 is pressurized for nearly full area usage of the activated carbon of the third filter element 44. This allows flowing the smoke evacuation gas through the activated carbon filter element 44 within the filter cartridge 24 to filter at least one of smoke, particulate, and impurities from the smoke evacuation gas.

A peripheral rim 64 is defined around the separator wall 56, wherein the third filter element 44 seats against the peripheral rim 64 to maintain spacing for the plenum 62 defined inside a volume defined between the separator wall 56 and the third filter element 44 and within the peripheral rim 64. A seal 66 is seated between the separator wall 56 and the third filter element 44 to force gas flow from the plenum 62 through the third filter element 44. A seal seat 68 is defined in the peripheral rim 64 with the seal 66 seated therein.

Another embodiment of a filter with tube set in accordance with this disclosure includes an adapter that plugs the pressure line, e.g., by plugging opening 54b, which is responsible for creating the gas seal described above. In this embodiment, a bi-lumen tube set would be attached to the filter cartridge, e.g., with one lumen connected to opening 54a and one lumen connected to opening 54c, with one lumen responsible for sense/insufflation gas, and the other lumen removing surgical gas and smoke from the cavity. This embodiment omits the third lumen of the tri-lumen tube set 36.

Figure 5:
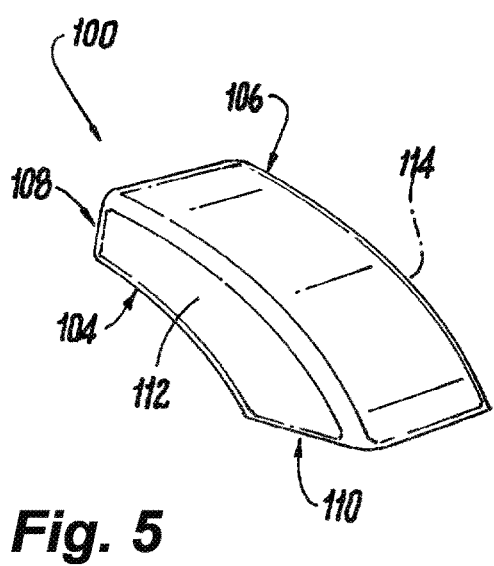
FIG. 5 is a schematic perspective view of a portion of the filter cartridge of FIG. 4, showing the cross-sectional shape of the humidity filter element.

With reference now to FIG. 5, a humidity filter element 100 is included in the evacuation/return flow path for removing humidity from an evacuation/return lumen of a tube set. The humidity filter element 100 includes a sintered polymer material configured to provide tortuous flow paths therethrough to condense humidity out of a flow through the humidity filter element 100. The sintered polymer material provides a tortuous flow path, but the porosity gives low resistance pathways through the humidity filter element 100. The gas can pass freely through the humidity filter element 100 but the polymer grains of the filter material alter the direction of gas flowing therethrough, creating physical obstacles that knock water vapor out of the gas flow and cause the humidity to condense on the surfaces of the filter material and drip downward for collection, preventing the condensed liquid from entering the interior of the system 10. With the humidity filter element 100 in-line within the gas path, there is no need for a pneumatic seal around the humidity filter element 100. The humidity filter element 100 still functions to condense moisture even if some of the gas flow passes around the humidity filter element 100.

Figure 6:
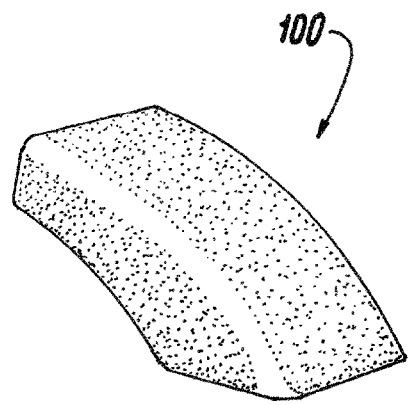
FIG. 6 is a perspective view of the humidity filter element of FIG. 5.

As indicated in FIGS. 2-4 and shown in cross-section in FIG. 4, the humidity filter element 100 is seated in a return passage of the filter housing 28 radially outboard of the first filter element 38a. The humidity filter element 100 has a cross-sectional shape that conforms to the return passage of the filter housing 28. Specifically, the return passage through the filter housing 28 includes a filter seat 102 that has the same cross-sectional shape as the humidity filter element 100. The cross-sectional shape of the humidity filter element 100 includes an inner radiused portion 104 and an outer radiused portion 106 (labeled in FIG. 5), wherein the inner and outer radiused portions 104, 106 are non-concentric, i.e., the distance between the inner and outer radiused portions 104 and 106 varies rather than being constant. The cross-sectional shape of the humidity filter element 100 also includes a circumferentially spaced apart set of radial ends 108 and 110. The upstream and downstream surfaces 112 and 114 of the humidity filter element 100 are planar and parallel to one another. FIG. 6 shows the humidity filter element 100 with the surface symbolically marked to indicate the surface (and internal) porosity.

Figure 7:
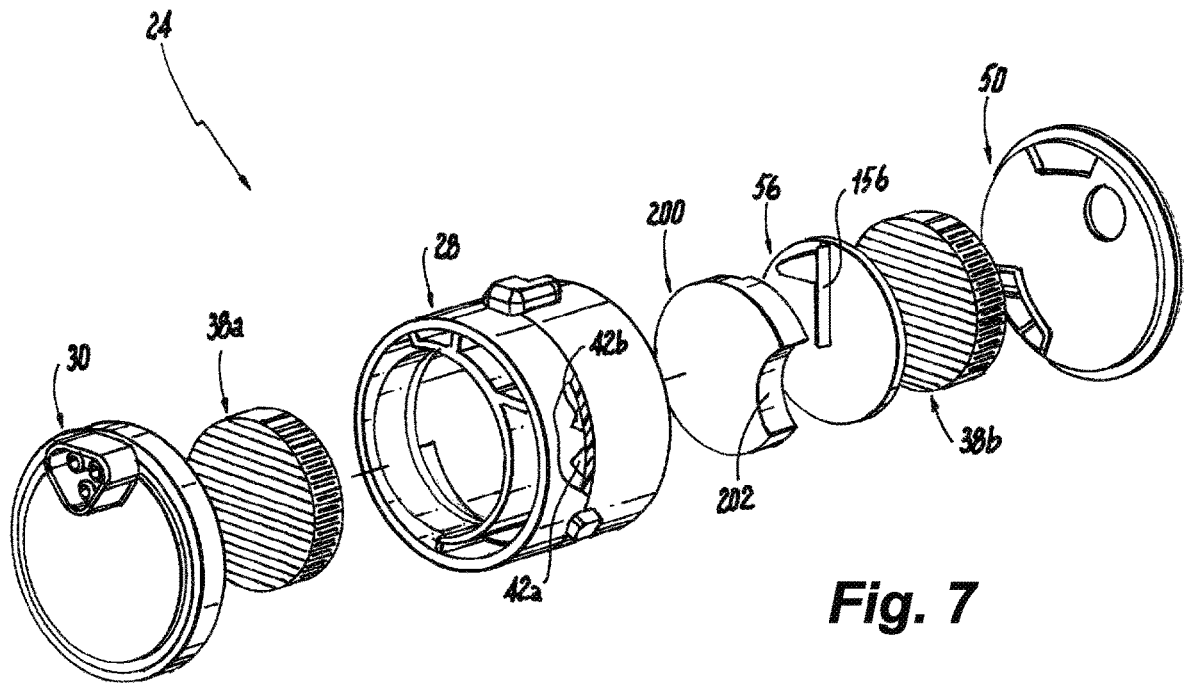
FIG. 7 is a partially cut-away exploded perspective view of another exemplary embodiment of a filter cartridge constructed in accordance with the present disclosure, showing a humidity filter element that seats between the pleated filter elements looking toward the openings in the fitting for the tri-lumen-tube set in the first cover plate.
Figure 8:
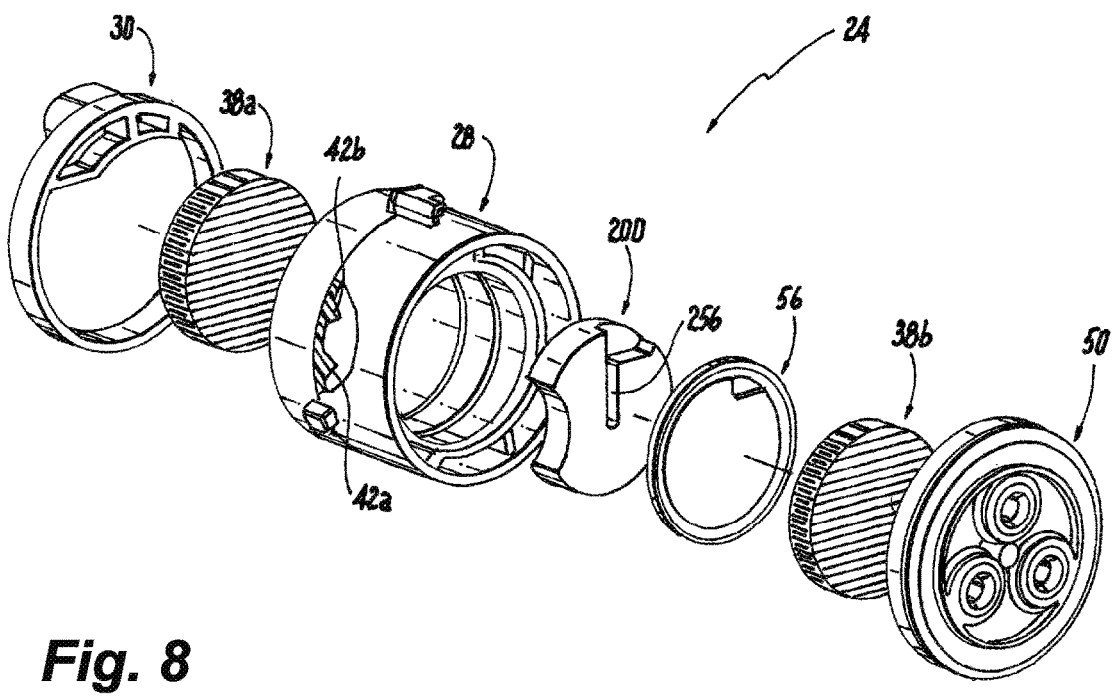
FIG. 8 is a partially cut-away exploded perspective view of the filter cartridge of FIG. 7, showing the filter cartridge components looking toward the apertures in the second cover plate that seal against the gas ports in the filter cartridge interface of FIG. 1.
Figure 9:
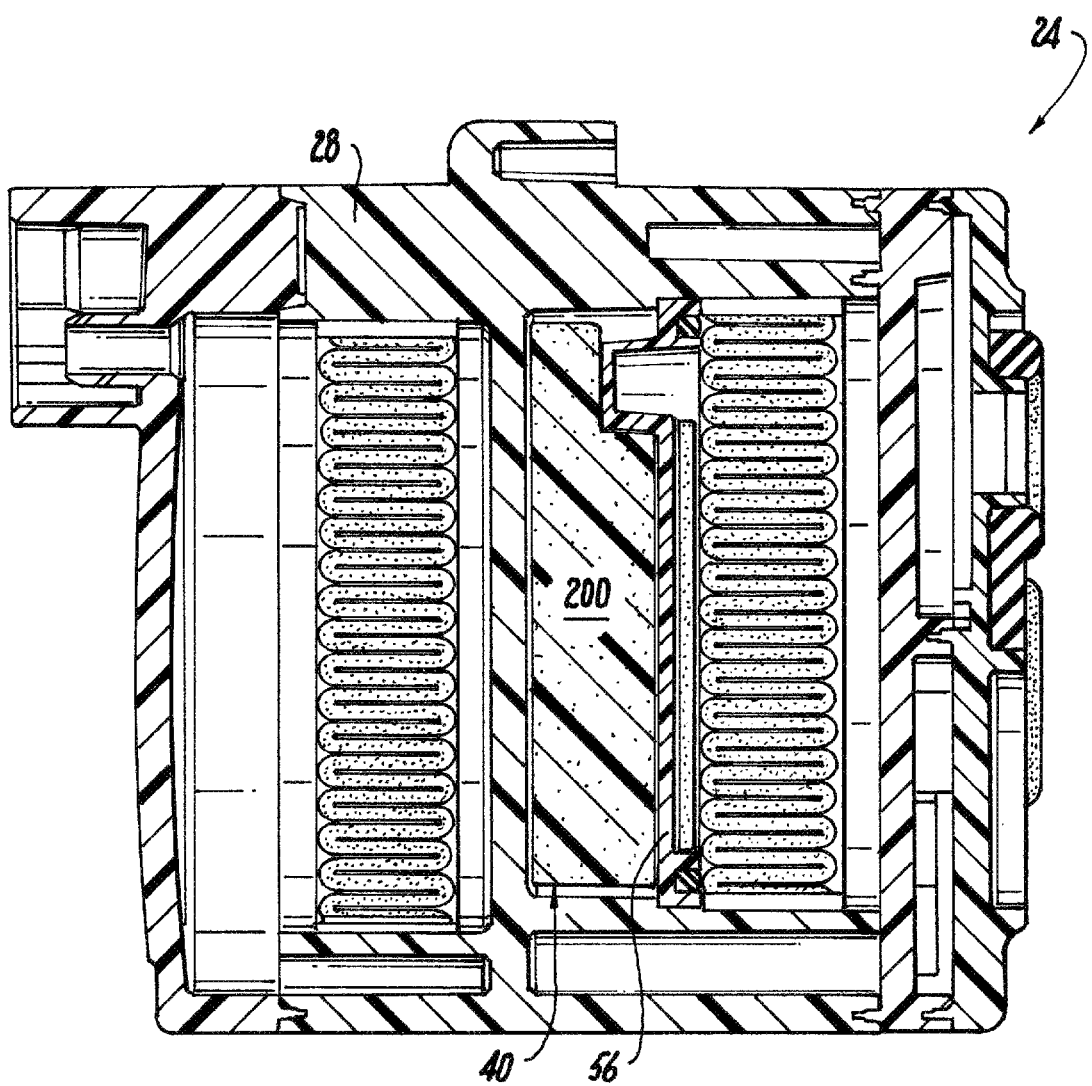
FIG. 9 is a cross-sectional side elevation view of the filter cartridge of FIG. 7, showing the filter elements assembled into the filter housing.
Figures 10, 11:
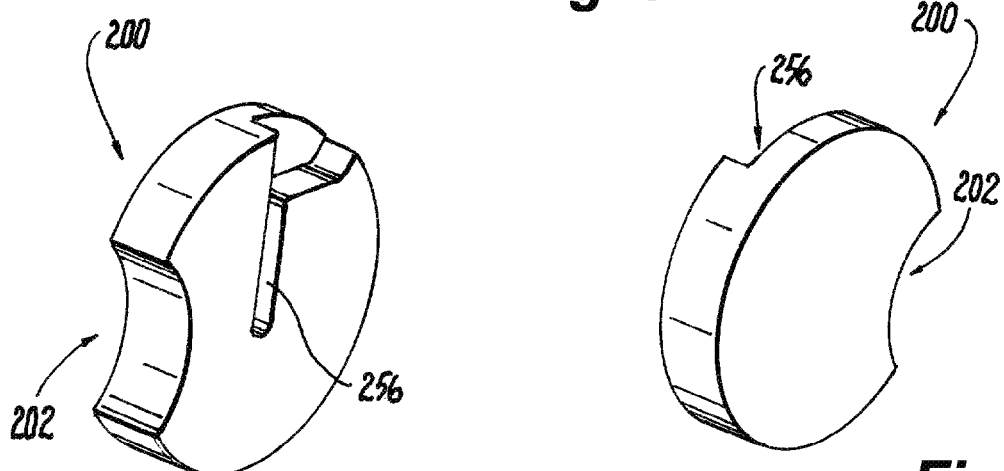
FIGS. 10 and 11 are perspective views from two opposed sides of the humidity filter element of FIG. 8.

With reference now to FIGS. 7-8, another exemplary embodiment of a humidity filter element 200 is shown similar to humidity filter element 100 described above, but wherein the humidity filter element 200 is seated in the filter housing 28 between the first and second filter elements 38a and 38b. As shown in FIG. 9, the separator wall 56 is positioned within the filter housing 28 between the humidity filter element 200 and the second filter element 38b. The filter housing 28 includes a pair of optical prisms 42a and 42b, shown in FIGS. 7-8, formed integral with the housing 28 within the reservoir of the fluid trap 40 for sensing level of a liquid in the reservoir. Optical prisms for sensing level of a liquid in a reservoir of a filter cartridge are described in U.S. Pat. No. 9,950,127 which is incorporated by reference herein in its entirety. The humidity filter element 200 and the separator wall 56 are keyed to one another for circumferential alignment, wherein the key 156 of the separator wall 56 is keyed to the depression 256 (labeled in FIGS. 10-11) in the humidity filter element 200. The humidity filter element 200 defines a lunate shaped notch 202, also identified in FIGS. 10-11, along one side thereof for accommodating the optical prisms 42a and 42b. Even with the humidity filter element 200 taking up most of the fluid trap 40 if liquids build up in the bottom of the fluid trap 40, as oriented in FIG. 9, the notch 202 provides room for the optical prisms 42a and 42b to function for detecting the liquids. Just as the humidity filter element 100 can be used with a tri-lumen or bi-lumen tube set, so the humidity filter element 200 can be used with either a tri-lumen or bi-lumen tube set. Additional details regarding tri-lumen and bi-lumen tube sets are found un U.S. Pat. No. 9,526,886 and U.S. Patent Application Publication No. 2017/0050011, each of which is incorporated by reference herein in its entirety.

Figures 12, 13:
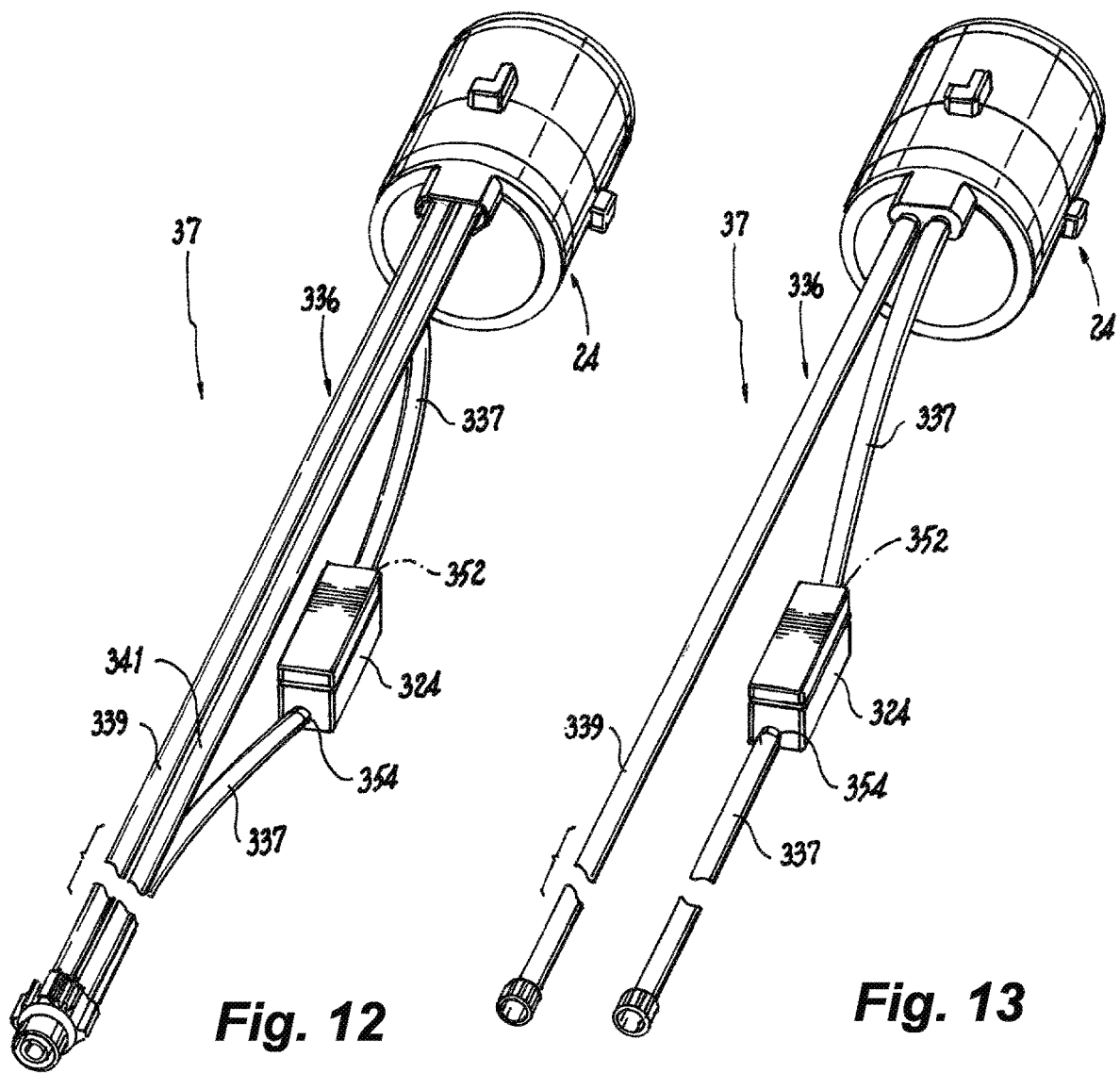
FIG. 12 is a perspective view of an exemplary embodiment of a humidity filter assembly constructed in accordance with the present disclosure, showing the humidity filter assembly connected in-line with one lumen of a tri-lumen tube set connected to a filter cartridge for connecting to a filter cartridge interface as shown in FIG. 1.
FIG. 13 is a perspective view of the humidity filter assembly of FIG. 12, showing the humidity filter assembly connected in-line with one lumen of a bi-lumen tube set connected to a filter cartridge for connecting to a filter cartridge interface as shown in FIG. 1.

With reference now to FIG. 12, a tube set assembly 37 for surgical gas delivery systems includes a filter cartridge 24 as described above but not necessarily including a humidity filter element 100 or 200 therein. The tube set 336 includes a first lumen 337 in fluid communication with the evacuation/return flow path of the filter cartridge 24 and a second lumen 339 in fluid communication with the insufflation and sensing flow path of the filter cartridge 24. The third lumen 341 can be in fluid communication with the third flow path through the filter cartridge 24 for providing pressurized gas supply to and from a pneumatic seal in a valve-less trocar, for example. An in-line humidity filter assembly 324 with a humidity filter housing 328 (labeled in FIG. 14) defines an inlet 354 in fluid communication with a first portion of the first lumen 337 for receiving gas from a patient and an outlet 352 in fluid communication with a second portion of the first lumen 337 for communication of humidity filtered gas from the in-line humidity filter assembly 324 to the filter cartridge. As shown in FIG. 12, the humidity filter assembly 324 can similarly be incorporated in-line with the return line 337 where tube set 336 is a bi-lumen tube set that omits the third lumen 341 and uses the second lumen 339 for insufflation and sensing. In this case, the filter cartridge 24 can be modified to block one port as described above.

Figure 14:
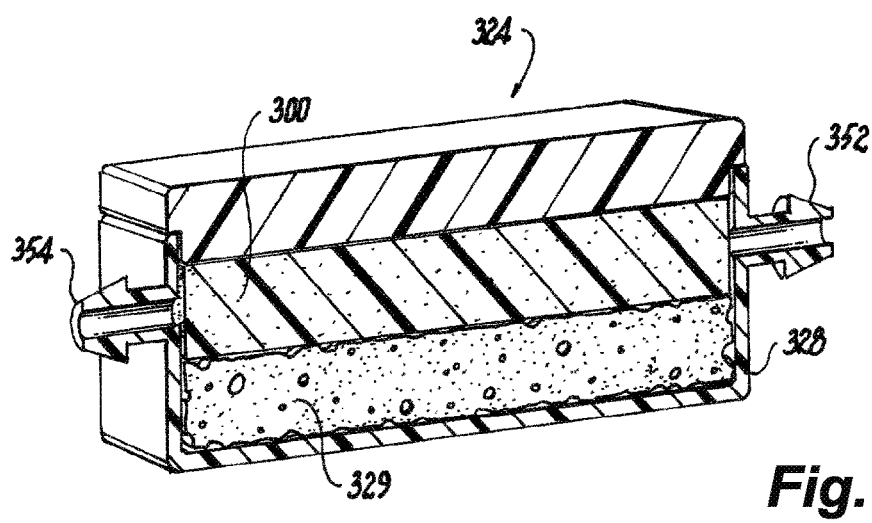
FIG. 14 is a cross-sectional perspective view of the humidity filter assembly of FIG. 12, showing the humidity filter element and the sponge element as planar layers.

As shown in FIG. 14, the humidity filter element 300, e.g., of the same sintered polymer material described above with respect to humidity filter elements 100 and 200, is seated in the humidity filter housing 328 for removing humidity from the first lumen 337 of the tube set 336. The humidity filter element 300 is in-line between the inlet 354 and the outlet 352 of the humidity filter housing 328 so gas passing through the humidity filter housing 328 must pass through the humidity filter element 300. A sponge element 329 is included within the humidity filter housing 328 offset from being in-line between the inlet 354 and outlet 352 of the humidity filter housing 328 for absorbing condensation from the humidity filter element, e.g., as gravity pulls liquid water from the humidity filter element 300 downward into the sponge element 329 if the humidity filter housing 328 is oriented as shown in FIG. 14. The humidity filter element 300 and the sponge element 329 form planar layers in parallel with one another.

Figures 15, 16:
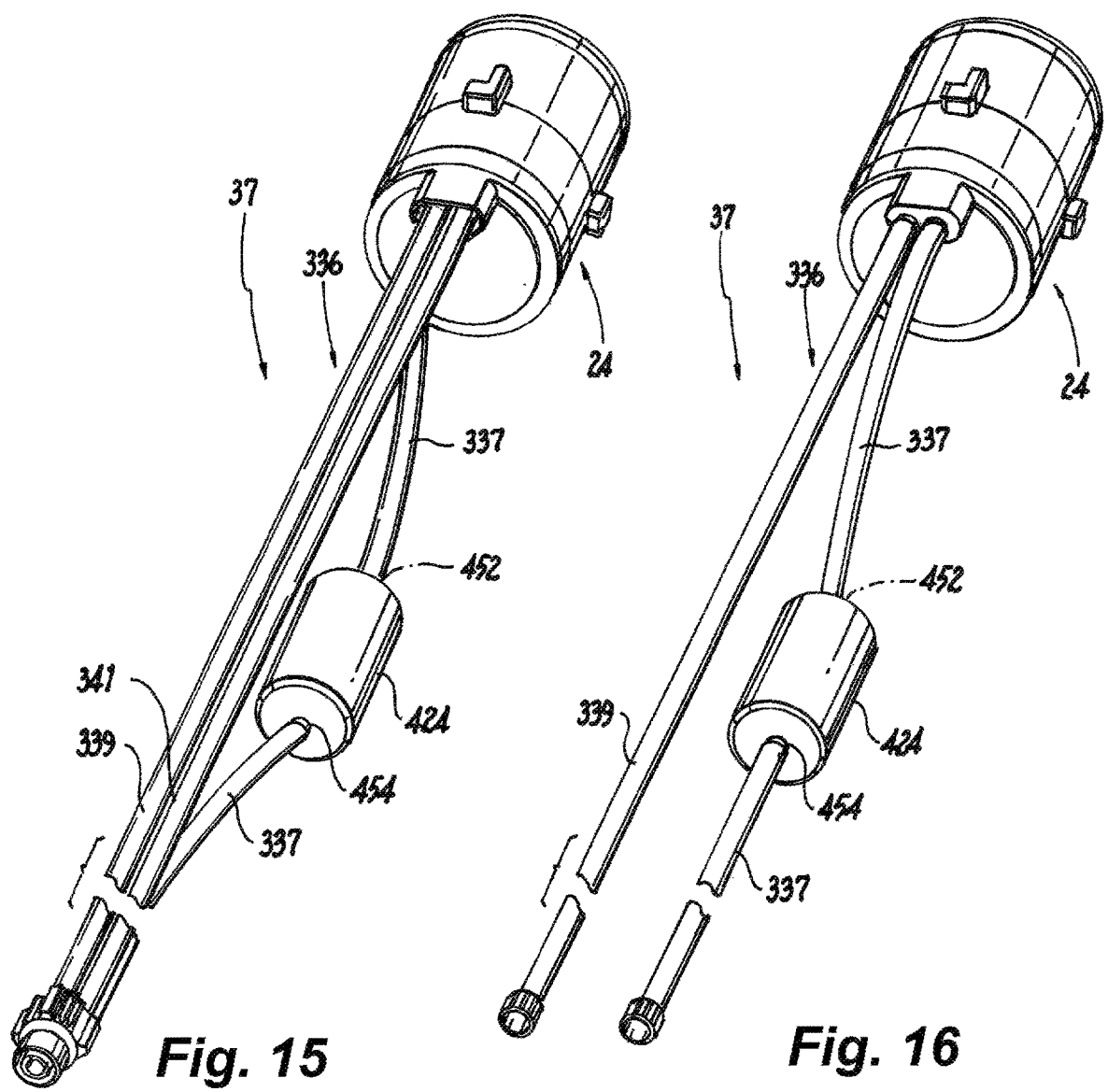
FIG. 15 is a perspective view of an exemplary embodiment of a humidity filter assembly constructed in accordance with the present disclosure, showing the humidity filter assembly connected in-line with one lumen of a tri-lumen tube set connected to a filter cartridge for connecting to a filter cartridge interface as shown in FIG. 1.
FIG. 16 is a perspective view of the humidity filter assembly of FIG. 15, showing the humidity filter assembly connected in-line with one lumen of a bi-lumen tube set connected to a filter cartridge for connecting to a filter cartridge interface as shown in FIG. 1.
Figure 17:
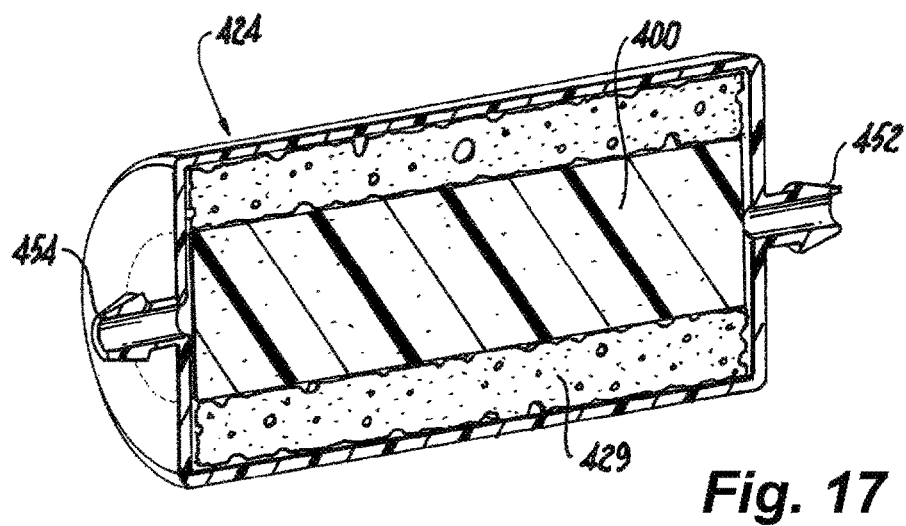
FIG. 17 is a cross-sectional perspective view of the humidity filter assembly of FIG. 15, showing the cylindrical humidity filter element and the sponge element as an annular layer arranged about the humidity filter element.

With reference now to FIGS. 15-16, another embodiment of a humidity filter assembly 424 can be used in-line with lumen 337 in the tri-lumen configuration, shown in FIG. 15, or bi-lumen configuration, shown in FIG. 16, of the tube set 336 as described above with respect to the humidity filter assembly 324. The humidity filter element 400 is cylindrical, and is of the same material described above with respect to humidity filter elements 100, 200, and 300. The sponge element 429 is an annular layer arranged around the humidity filter element 400, as indicated with the hidden lines in FIG. 17. The humidity filter element 400 is in-line between the inlet 454 and the outlet 452 of the humidity filter housing 428 so gas passing through the humidity filter housing 428 must pass through the humidity filter element 400. The sponge element 429 is included within the humidity filter housing 428 offset from being in-line between the inlet 454 and outlet 452 of the humidity filter housing 428 for absorbing condensation from the humidity filter element. With this geometry, the humidity filter housing 428 does not need to be oriented any particular way relative to the direction of the force of gravity, since the sponge element 429 can absorb liquid from the humidity filter element 400 from essentially any direction.

With reference now to FIGS. 18-19, another embodiment of a humidity filter assembly 524 can be used in-line with lumen 337 in the tri-lumen configuration, shown in FIG. 18, or bi-lumen configuration, shown in FIG. 19, of the tube set 336 as described above with respect to humidity filter assembly 324. The humidity filter housing 528 includes a drain 555 which can in turn be connected to a drain tube 556 connected to a drainage or waste collection system 557 for removal of condensation from the humidity filter housing 528. As shown in FIG. 20, the humidity filter housing 528 includes only the humidity seal element 500 and is devoid of a separate sponge element.

The methods and systems of the present disclosure, as described above and shown in the drawings, provide for filtration of surgical gases with superior properties including improved removal of smoke, particulate, and impurities. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A filter cartridge for surgical gas delivery systems comprising:
    a filter housing configured to be seated in a filter cartridge interface of a surgical gas delivery system, with a plurality of flow paths defined through the filter housing including at least one evacuation/return flow path and at least one insufflation/sensing flow path;
    a first filter element seated in a first end portion of the filter housing; and
    a second filter element seated in a second end portion of the filter housing opposite the first end portion; and
    a humidity filter element in the at least one evacuation/return flow path for removing humidity from an evacuation/return lumen of a tube set, wherein the humidity filter element includes a sintered polymer material configured to provide tortuous flow paths therethrough to condense humidity out of a flow through the humidity filter element, wherein the humidity filter element is seated in a return passage of the filter housing radially outboard of the first filter element and includes a cross-sectional shape that conforms to the at least one evacuation/return flow path of the filter housing, wherein the humidity filter element extends along an axial length of the filter housing beyond the first filter element.

2. The filter cartridge as recited in claim 1, wherein each of the first and second filter elements includes a pleated filter material.

3. The filter cartridge as recited in claim 1, further comprising an activated carbon filter element seated in the filter housing between the humidity filter element and the second filter element.

4. The filter cartridge as recited in claim 1, wherein the cross-sectional shape of the humidity filter element includes an inner radiused portion and an outer radiused portion, wherein the inner and outer radiused portions are non-concentric.

5. The filter cartridge as recited in claim 4, wherein the cross-sectional shape of the humidity filter element includes a circumferentially spaced apart set of radial ends.

6. A filter cartridge for surgical gas delivery systems comprising:
- a filter housing configured to be seated in a filter cartridge interface of a surgical gas delivery system, with a plurality of flow paths defined through the filter housing including at least one evacuation/return flow path and at least one insufflation/sensing flow path;
- a first filter element seated in a first end portion of the filter housing;
- a second filter element seated in a second end portion of the filter housing opposite the first end portion;
- a humidity filter element in the at least one evacuation/return flow path for removing humidity from an evacuation/return lumen of a tube set, wherein the humidity filter element includes a sintered polymer material configured to provide tortuous flow paths therethrough to condense humidity out of a flow through the humidity filter element, wherein the humidity filter element is seated in the filter housing between the first and second filter elements;
- a separator wall within the filter housing between the humidity filter element and the second filter element, wherein the separator wall includes a gas aperture therethrough, wherein a fluid trap is defined between the first filter element and the separator wall, wherein the gas aperture is configured to allow passage of gas above a reservoir of fluid trapped in the fluid trap, wherein the humidity filter element and the separator wall are keyed to one another for circumferential alignment, wherein the humidity filter element defines a lunate notch along one side thereof for accommodating at least one optical prism formed integral with the housing within the reservoir for sensing level of a liquid in the reservoir.

7. The filter cartridge as recited in claim 6, wherein the filter housing includes at least one optical prism formed integral with the housing within the reservoir for sensing level of the liquid in the reservoir.

8. The filter cartridge as recited in claim 6, wherein a cover plate includes: a tri-lumen tube set connected to a fitting for connecting the tri-lumen tube set for communication of gases between the tri-lumen tube set and the filter elements.

9. The filter cartridge as recited in claim 6, wherein a cover plate includes: a bi-lumen tube set connected to a fitting for connecting to the bi-lumen tube set for communication of gases between the bi-lumen tube set and the filter elements.

10. A tube set assembly for surgical gas delivery systems comprising:
- a filter cartridge with a filter housing configured to be seated in a filter cartridge interface of a surgical gas delivery system, with a plurality of flow paths defined through the filter housing including at least one evacuation/return flow path and at least one insufflation/sensing flow path;
- a tube set including a first lumen in fluid communication with the at least one evacuation/return flow path and a second lumen in fluid communication with the at least one insufflation/sensing flow path;
- an in-line humidity filter assembly with a humidity filter housing defining an inlet in fluid communication with a first portion of the first lumen for receiving gas from a patient and an outlet in fluid communication with a second portion of the first lumen for communication of humidity filtered gas from the in-line humidity filter assembly to the filter cartridge; and
- a humidity filter element seated in the humidity filter housing for removing humidity from the first lumen of the tube set, wherein the humidity filter element includes a sintered polymer material configured to provide tortuous flow paths therethrough to condense humidity out of a flow through the humidity filter element, wherein the humidity filter element is in-line between the inlet and the outlet of the humidity filter housing, wherein the humidity filter element extends axially from the inlet to the outlet of the humidity filter housing.

11. The assembly as recited in claim 10, further comprising a sponge element within the humidity filter housing offset from being in-line between the inlet and outlet of the humidity filter housing for absorbing condensation from the humidity filter element.

12. The assembly as recited in claim 11, wherein the humidity filter element is a planar layer, and wherein the sponge element is a planar layer in parallel with the humidity filter element.

13. The assembly as recited in claim 11, wherein the humidity filter element is cylindrical, and wherein the sponge element is an annular layer arranged around the humidity filter element.

14. The assembly as recited in claim 10, wherein the humidity filter housing includes a drain for removal of condensation from the humidity filter housing, wherein the humidity filter housing includes only the humidity seal element and is devoid of a separate sponge element.

15. The assembly as recited in claim 10, wherein the tube set is a bi-lumen tube set.

16. The assembly as recited in claim 10, wherein the tube set is a tri-lumen tube set.

* * * * *